United States Patent [19]

Ikuta et al.

[11] Patent Number: 5,569,594
[45] Date of Patent: Oct. 29, 1996

[54] TRANSESTERIFICATION WITH LIPASE IMMOBILIZED ON A POLYMER CONTAINING EPOXY AND TERTIARY AMINO GROUPS

[75] Inventors: Yuzo Ikuta, Yokosuka; Satoshi Tashiro, Yokohama; Yoshiyuki Hatano, Yokohama; Tadasu Fujita, Yokohama; Noboru Andoh, Yokohama; Sachio Asaoka, Yokohama; Haruto Kobayashi, Yokohama; Takeshi Minami, Yokohama, all of Japan

[73] Assignees: The Nisshin Oil Mills, Ltd., Tokyo; Chiyoda Corporation, Yokohama, both of Japan

[21] Appl. No.: 438,921

[22] Filed: May 10, 1995

Related U.S. Application Data

[62] Division of Ser. No. 65,496, May 24, 1993, Pat. No. 5,445,955.

[30] Foreign Application Priority Data

May 25, 1992 [JP] Japan ................. 4-132475

[51] Int. Cl.$^6$ .............. C12P 7/64; C12P 7/62; C12N 11/08; C12N 11/06
[52] U.S. Cl. ............ 435/134; 435/135; 435/180; 435/181; 435/198
[58] Field of Search .............. 435/134, 174, 435/177, 180, 181, 182, 198, 135

[56] References Cited

U.S. PATENT DOCUMENTS

| | | | |
|---|---|---|---|
| 4,210,723 | 7/1980 | Dorman et al. | 435/180 |
| 4,239,854 | 12/1980 | Hirohara et al. | 521/31 |
| 5,102,799 | 4/1992 | Urban et al. | 435/180 |
| 5,232,843 | 8/1993 | Bosley et al. | 435/135 |

FOREIGN PATENT DOCUMENTS 0322213  6/1989  European Pat. Off. .

*Primary Examiner*—David M. Naff
*Attorney, Agent, or Firm*—Oblon, Spivak, McClelland, Maier & Neustadt, P.C.

[57] ABSTRACT

Transesterification involving a fat, or a fat and fatty acid, or a phospholipid is carried out with a lipase or phospholipase immobilized on a polymer carrier. The transesterification is preferably carried out in a system containing a very small amount of water such as 50 to 2,000 ppm. The phospholipase can be phospholipase $A_2$. In a first embodiment, lipase from a microorganism of the genus Rhizopus, Mucor, Alcaligenes or Candida is immobilized on the surface of a hydrophobic, insoluble organic polymer carrier having pores of an average diameter of 10 nm or larger and having on the surface epoxy groups capable of covalently binding lipase. The immobilized lipase is dried under reduced pressure. In a second embodiment, lipase is immobilized on the surface of a polymer carrier such as a hydrophobic, insoluble organic polymer carrier having a pore diameter of 5 to 1,000 nm and having on the surface a functional group capable of binding lipase and an anion-exchange group. Preferably, the functional group is an epoxy group and the anion-exchange group is a tertiary amino group. The lipase may be obtained from the same microorganism as in the first embodiment or from another lipase-producing microorganism. Iramobilization can be carried out as in the first embodiment. It is preferred to contact a solution of lipase with the polymer carrier in the presence of a fatty acid or derivative thereof for 10 minutes to 10 hours to covalently bond the lipase to the polymer carrier.

21 Claims, No Drawings

TRANSESTERIFICATION WITH LIPASE IMMOBILIZED ON A POLYMER CONTAINING EPOXY AND TERTIARY AMINO GROUPS

This is a divisional application of Ser. No. 08/065,496 filed May 24, 1993, now U.S. Pat. No. 5,445,955.

BACKGROUND OF THE INVENTION

The present invention relates to an immobilized lipase or phospholipase which is suitable for transesterification of oils and fats or phospholipids, a process for producing it and a process for transesterifying oils and fats or phospholipids with the immobilized lipase or phospholipase.

The transesterification reaction is an important means for the production of wax esters, fatty acid esters, saccharide esters, steroids and the like or for modifying vegetable oils and animal oils. when a lipase which is an enzyme for decomposing oils and fats is used as a catalyst in the transesterification reaction, this reaction can be conducted under mild conditions and, in addition, the intended product can be efficiently produced according to the substrate specificity and site specificity thereof. It was proposed to conduct the transesterification reaction in the presence of a lipase in an amount sufficient for expressing the enzymatic activity while water content of the reaction system is reduced.as far as possible. However, it is difficult to homogeneously disperse the lipase in a system containing very small amount of water (oily system), since lipase is soluble in water.

To solve this problem, an immobilized lipase comprising a lipase carted on an insoluble carrier is used. By employing the immobilized lipase, there can be obtained advantages in that the separation of the product is further facilitated, the repeated use of the lipase is made possible and the continuation of the reaction is also facilitated.

However, although the immobilized lipase has the above-described advantages, no immobilized lipase which is practically usable has been obtained.

Carriers heretofore proposed for the production of the immobilized lipase include porous chitosan moldings [Japanese Patent Unexamined Published Application (hereinafter referred to as "J.P. KOKAI") No. 59-213390], macroporous anion exchange resins (J.P. KOKAI No. 60-98984), macroporous phenolic adsorbent resins (J.P. KOKAI No. 61-20268), animal bones (J.P. KOKAI No. 64-80286), products obtained by uaking foaming phenolic resins (J.P. KOKAI No. 2-100678), hydrophobic carriers having pore diameter of at least 50 nm (J.P. KOKAI No. 2- 138986), cation exchange resins (J.P. KOKAI No. 3-64185) and macroporous acrylic adsorbent resins (J.P. KOKAI No. 3-501922). However, a sufficient lipase activity cannot be obtained by using such a carrier. J.P. KOKAI No. 60-137290 discloses a process for immobilizing an enzyme on a polysaccharide carrier by means of an aldehyde group formed by oxidation of a hydroxyl group of the polysaccharide. However, this process is unsuitable for reactions in a system containing very small amount of water, since the carrier is hydrophilic. Although a process for immobilizing an enzyme on a chelate resin is disclosed in J.P. KOKAI No. 1-262795, an activity sufficient for the practical use has not yet been obtained.

SUMMARY OF THE INVENTION

A primary object of the present invention is to provide a lipase immobilized on a carrier, which exhibits an excellent lipase activity, which is suitable for use for the transesterification reaction in a system containing very small amount of water and which is usable in a reduced amount.

Another object of the invention is to provide a lipase or phospholipase immobilized on a carrier, which exhibits an excellent lipase or phospholipase activity, which is suitable for use for the transesterification reaction in a system containing very small amount of water and which has good duration of life.

Another object of the present invention is to provide a process for efficiently producing the immobilized lipase or phospholipase.

Another object of the present invention is to provide a process for transesterifying oils and fats or phospholipids with the immobilized lipase or phospholipase.

These and other objects of the present invention will be apparent from the following description and Examples.

The present inventions have been completed on the basis of a finding that the above-described objects can be attained by supporting a specified lipase on a specified carrier comprising a macroporous adsorbent resin having an epoxy group on the surface thereof, or by supporting a lipase or phospholipase on a specified carrier comprising a macroporous adsorbent resin having a functional group capable of binding a lipase or phospholipase in an aqueous solution and an anionexchange group on the surface thereof.

Namely, the first aspect of the present invention provides an immobilized lipase for transesterification of oils and fats which comprises a lipase selected from the group consisting of those derived from Rhizopus, Mucor, Alcaligenes and Candida genus and immobilized on the surface of a carrier comprising a hydrophobic, insoluble organic polymer having pores of an average diameter of 10 nm or larger and epoxy group on the surface thereof.

The second aspect of the present invention provides an immobilized lipase or phospholipase which comprises a lipase or phospholipase immobilized on the surface of a polymer carrier having a functional group capable of binding a lipase or phospholipase in an aqueous solution and an anion-exchange group on the surface thereof.

The present invention further provides a process for producing an immobilized lipase or phospholipase which comprises the steps of bringing the carrier into contact with an aqueous solution of the above-described lipase or phospholipase so that the lipase or phospholipase is carried by the carrier by means of a covalent bond and then drying the resultant product.

The present invention further provides a process for transesterifying oils and fats or phospholipids which comprises the step of transesterifying an oil and fat or phospholipids in the presence of the above-described immobilized lipase or phospholipase.

DESCRIPTION OF THE PREFERRED EMBODIMENTS

The first aspect of the invention will be described below.

Examples of the hydrophobic insoluble organic polymers forming the carrier in the present invention include copolymers of divinylbenzene and copolymerizable monomer such as styrene, acrylic ester, methacrylic ester, and methacrylic ester resins, acrylic ester resins, polypropylenes, nylons and phenolic resins. Among these, the styrene/divinylbenzene copolymers, (meth)acryl ester/divinylbenzene copolymers and a mixture thereof are particularly preferred. The pore diameter of the resins is at least 10 nm, preferably 10 to 1,000 nm.

It is preferred in the present invention to bond the epoxy functional group with the insoluble organic polymer constituting the carrier through an alkyl chain or aryl chain so that the epoxy functional group is positioned on the surface of the carrier comprising the hydrophobic insoluble organic polymer. The epoxy group can be of any type, and is preferably a 1,2-epoxido group in which oxygen is bonded with carbon atoms which are adjacent to each other. The number of carbon atoms of the alkyl chain adjacent to the epoxido is 1 to 20, preferably 1 to 10. In this case, the alkyl chain can be replaced with an aryl chain. The number of the benzene nucleus (or nuclei) is 1 to 10, preferably 1 to 3. These functional groups can be introduced into the above-described adsorbent resin (or the adsorbent resin which has been pretreated to have a functional group) by an ordinary chemical bond method such as ester bond method or copolymerization reactions such as reacting methacrylic glycide with divinylbenzene. It is also possible to use a commercially available resin into which an epoxy functional group has been previously incorporated. Such commercially available resins include Lewatit (® Lewatit) R259K of Bayer and FP 4000 of Japan Organo Co., Ltd.

Although the particle diameter of the carrier used in the present invention is not particularly limited, it is preferred that at least 90% of the carrier particles have a diameter of 50 to 1,000 μm, particularly an average diameter of 300 to 600 μm.

The lipase to be immobilized on the carrier is one or more lipases selected from the group consisting of those derived from Rhizopus, Mucor, Alcaligenes and Candida genus. The intended immobilized lipase having a high activity has not been obtained prior to the present invention wherein such a specifed lipase is immobilized In these lipases, those derived from Mucor or Rhizopus genus are particularly preferred. The preferred transesterification activity of the immobilized enzyme is at least 150 units per gram (dry weight) of the immobilized enzyme.

The description will be made on the process for producing the immoblized lipase.

In the present invention, the lipase is supported on the carrier by bringing a porous, insoluble carrier comprising a hydrophobic matrix having an epoxy group introduced thereinto into contact with an enzyme solution. The amount of the lipase solution varies depending on the variety of the lipase used. For example, preferably 1 to 200 parts by weight of an aqueous solution containing 0.05 to 10% by weight of the lipase is used per part by weight (on dry basis) of the carrier. In this step, a gentle stirring is desirable. The time required for the immobilization is 10 min to 40 hours, preferably 4 to 24 hours. The immobilization temperature ranges from 4° to 50° C., preferably 5° to 25° C. If necessary, the pH of the enzyme solution can be adjusted with a buffer solution to preferably around an optimum pH for the enzyme. When lipase is used, the pH is adjusted preferably to an optimul pH for the hydrolysis activity determined by using the free enzyme, such as pH 5 to 9. The variety of the buffer solution is not particularly limited. An acetic acid buffer solution, phosphoric acid buffer solution or the like can be used. The carrier carrying the enzyme is subjected to, for example, filtration to remove the remaining solution and, if necessary, washed with ion-exchanged water or the like. It is also possible to block the unreacted epoxy group remaining in the carrier by using an aqueous solution of an amino group-containing substance suck as tris hydrochloride buffer solution as the washing solution. The immobilized enzyme thus dehydrated is preferably dried by, for example, drying under reduced pressure to a water content of desirably 0.5 to 30% by weight, preferably 5 to 10% by weight. When the water content after drying is below 0.5%, the sufficient transesterification activity cannot be exhibited and, on the contrary, when it is above 30%, the deactivation is caused and hydrolysis occurs as a side reaction to an sxtent which is not negligible. The ratio of the carrier to the enzyme used in the immobilization is such that 0.1 to 10 g, preferably 0.2 to 5 g, of protein in the enzyme is carried by 1 g (on dry basis) of the carrier. However, the ratio is not particularly limited.

Since the enzyme to be immobilized contains a large amount of proteins as impurities, it is important for obtaining the immobilized enzyme of a high activity that the intended lipase which is a protein is selected to some extent from these impurities in the immobilization step and that the enzyme thus carried effectively exhibits the transesterification activity. These important factors can be determined by the degree of concentration and expression efficiency defined as follows:

> Degree of concentration=(hydrolysis activity per protein carried by carrier)/[hydrolysis activity per protein of enzyme subjected to immobilization (specific activity)], and > Expression efficiency=(transesterification activity per weight of carrier)/(hydrolysis activity of carried enzyme per weight of carrier).

There are various methods for determining the hydrolysis activity. The method employed herein is as follows: a solution prepared by mixing 1 part by weight of olive oil (The Pharmacopoeia of Japan) with 1.5 parts by weight of 2% aqueous PVA solution (18.5 g/l of Poval 117 produced by Kuraray Co., Ltd. and 1.5 g/l of Poval 205) and emulsifying the solution is used as the substrate. 4 ml of a McIlvaine's buffer solution (pH 7) and 1 ml of an enzyme solultion are added to 5 ml of the emulsion. The resultant mixture is reacted at 37° C. for 60 min. The hydrolysis activity is determined from the amount of free fatty acids formed by the hydrolysis. 1 unit is an activity which increases the free fatty acids in an amount of 1 μmol per min, which is calculated from the amount of free fatty acids formed by the hydrolysis.

There are various methods for determining the transesterification activity. The method employed herein is as follows: a solution of 50 mM of triolein (or palmolein), 50 mM of palmitic acid (or myristic acid) and 100 to 150 ppm of water in hexane was used as the substrate. 20 to 200 mg (dry basis) of the immobilized enzyme is added to the substrate and the reaction is conducted at 50° C. to determine the maximum reduction rate of palmitic acid (or myristic acid) concentration. 1 unit is an activity which reduces palmitic acid (or myristic acid) in an amount of 1 μmol per min, which is calculated from the maximum reduction rate.

The second aspect of the invention will be described below but the description about the first aspect of the invention can be applied to the second aspect of the invention except for the following description.

Examples of the hydrophobic insoluble organic polymers forming the carrier having a functional group capable of binding a lipase or phospholipase in an aqueous solution and an anion-exchange group on the surface thereof include polymers having a matrix comprising divinylbenzene copolymers, methacrylic ester resins, acrylic ester resins, polypropylenes, nylons, phenolic resins and the like. Among these, the divinylbenzene copolymers are particularly preferred. The pore diameter of the resins is 5 to 1000 nm, preferably 10 to 1,000 nm.

Examples of the functional group capable of binding a lipase or phospholipase in an aqueous solution includes an epoxy group, an cyanide group, an aldehyde group, a triazinyl group and the like. Among these, an epoxy group is preferable, and a 1,2-epoxido group in which an oxygen atom is bonded with carbon atoms adjacent to each other is more preferable.

Examples of the anion-exchange group include a primary amino group, a secondary amino group, a tertiary amino group, quaternary ammonium group and the like. Among these, diethylaminoethyl group (DEAE) and dimethylamino group which are tertiary amino groups showing weak-basicity are preferable.

The functional group capable of binding a lipase or phospholipase in an aqueous solution and the anion-exchange group are present on the surface of the carrier. A ratio of the functional group or the anion-exchange group to the carrier may be optional, but it is preferable that the ratio of the functional group or the anion-exchange group to the carrier be 0.2/1 to 5.0/1 (mole/kg), more preferably 0.5/1 to 2.0/1 (mole/kg), respectively. The functional group and the anionexchange group can be introduced into the polymer carrier by the conventional method, for example, by coexisting monomers having the functional group capable of binding a lipase or phospholipase in an aqueous solution or the anion-exchange group at the time of polymerization of the polymer carrier to copolymerize them or by pretreating the carrier polymer in such that reactive functional groups are formed on the surface of the carrier and introducing an intended functional group according to an ordinary chemical bond method such as ester bond method. Examples of the thus-obtained carriers having the functional group capable of binding a lipase or phcspholipase in an aqueous solution and the anion-exchange group include Lewatit (® Lewatit) R260K which is commercially available and another carriers such as carriers prepared in referential Example 1 mentioned below. Lewatit R260K has epoxy groups and secondary amino groups, whereas the polymer carrier in referential Example 1 has epoxy groups and tertiary amino groups which are more preferable.

In the second aspect of the invention, any lipase or phospholipase can be immobilized on the carrier and the lipase is not limited to the specific one as in the first aspect of the invention. Examples of lipases usable in the second aspect of the invention include those derived from Rhizopus, Mucor, Aspergillus, Alcaligenes, Geotrichum, Candida, Pseudomonas, Penicillium and Chromobacterium genus. Among these, lipases derived from Rhizopus and Mucor genus are preferable. Examples of phospholipases include phospholipase $A_1$ derived from animal brain, liver, pancreas tissues and Rhizopus genus, phospholipase $A_2$ derived from the same tissues, Escherichia and Microbacterium genus, and phospholipase B derived from the same tisses, Penicillium genus, wheat bran and rice bran.

Immobilized lipase or phospholipase of the second aspect of the invention can be prepared by the same method as in the first aspect of the invention. In this connection, it may be more preferable that the immobilized lipase or phospholipase is prepared by bring the polymer matrix into contact with an enzyme solution containing lipase or phospholipase in the presence of fatty acids or derivatives thereof. For example, the polymer carrier is pretreated with a fatty acid or its derivative and then brought into contact with an aqueous lipase solution (ph of 5 to 9) or an aqueous phospholipase solution (ph of 4 to 10) so as to immobilize the lipase or phospholipase onto the polymer carrier. Alternatively, fatty acid or its derivative is dispersed in an aqueous solution containing the polymer carrier and to the resultant is added a lipase or phospholipase, after which the resulting mixture is agitated for 10 minutes to 10 hours, preferably 10 minutes to 1 hour so as to uniformly immobilize the lipase or phospholipase onto the carrier. Thereafter, the resulting immobilized carrier is treated in the same manner as in the first aspect of the invention to obtain an end product of immobilized lipase or phosph0lipase. Examples of fatty acids or the derivatives include fats and oils such as rapeseed oil, soybean oil, corn oil, palm oil, fractional oils from these oils, fatty acid esters such as fatty acid monoglycerides or diglycerides, fatty acids such as oleic acid and lecithin. In this connection, it is preferable that the fatty acid or its derivative be the same as those used as a raw material to be subjected to transesterification reaction with the immobilized lipase or phospholipase. Among these, rapeseed oil, palm oil, fatty acids such as oleic acid and lecithin are preferable. The fatty acids or the derivatives are preferably added to the polymer carrier in an amount of 1 to 50 parts by weight, preferably 5 to 30 parts by weight relative to 100 parts by weight of the polymer carrier.

The transesterification of oils and fats or phospholipids can be efficiently conducted with the above-described immobilized lipase or phospholipase according to the first or second aspect of the present invention. The transesterification is particularly suitably conducted in a reaction system having a water content of 50 to 2,000 ppm, preferably as low as 100 to 1,000 ppm. The transesterification reaction is conducted at a temperature of preferably 30° to 70° C. and, if necessary, in an organic solvent in the present invention. The organic solvents used are those which do not impair the activity of the immobilized enzyme such as n-hexane and petroleum ethers. The oils and fats or phospholipids to be transesterified are ordinary fats and oils, lecithin and their derivatives, preferably vegetable oils, fats and fatty acids and, in addition, animal oils and fats, oils and fats produced from fishes and shellfishes and fatty acids produced from them. Specific examples thereof include palm oil, palm kernel oil, rapeseed oil, soybean oil, cotton seed oil, sesame oil, coconut oil, sunflower oil cocoa fat, olive oil, tallow, lard, processing oil such as fractinal oils and hydrogenated oils obtained from these oils, and a mixture thereof. Examples of fatty acids include saturated or unsaturated fatty acids having 6 to 22 carbon atoms such as caproic acid, captic acid, lauric acid, myristic acid, palmitic acid, stearic acid, oleic acid, linolenic acid, linoleic acid, behenic acid.

Several combinations of raw materials can be used in the transesterification reaction with the immobilized lipase or phospholipase of the present invention. For example, combinations of (one or more) fat and oil with fatty acid or its ester, or two or more fats and oils can be used in cases of using the immobilized lipase, combinations of lecithin with fatty acid or its ester can be used in cases of using the immobilized phospholipase, and combinations of lecithin with fat and oil can be used in cases of using a combination of immobilized lipase and phospholipase. Preferable examples of lecithin include mono or diacylglycerophospholipid such as phosphatidylcholine, phosphatidyl ethanolamine, phosphatidylinositol, phosphatidylserine, phosphatidic acid and their lyso form. These can be singly or in combination. In addition, fats and oils containing lecithin can be used.

The various transesterification reactions can be conducted for producing wax esters, fatty acid esters, saccharide esters and steroids or for modifying vegetable and animal oils.

The first aspect of the present invention thus provides the immobilized lipase having an extremely high lipase activity, suitable particularly for the transesterification reaction in a system containing very small amount of water and capable of reducing the amount of lipase used. The second aspect of the invention also provides the lipase or phospholipase immobilized on a carrier, which exhibits an excellent lipase or phospholipase activity, which is suitable for use for the transesterification reaction in a system containing very small amount of water and which has good duration of life. Therefore, the immobilized lipase or phospholipase of the present invention is industrially extremely important. By using the immobilized lipase or phospholipase, the transesterification of the oils and fats or phospholipids can be efficiently conducted.

The following Examples will further illustrate the present inventions.

EXAMPLE 1

1 g of lipase having 1,3-site specificity (Lipase F-AP 15 derived from *Rhizopus oryzae*; a product of Amano Seiyaku Kabushiki Kaisha) (210,000 hydrolysis unit/g) was dissolved in 50 ml of ion-exchanged water to prepare an enzyme solution. 5 g of a porous resin prepared by introducing epoxy groups into a matrix resin comprising styrene/divinylbenzene copolymer (Lewatit R259K having pore diameter of 17 nm and average particle diameter of 500 μm; a product of Bayer) (water content: about 60%) was added to the solution. The resulting mixture was gently shaken at 5° C. for 4 hours so that the lipase was carried by the resin by means of covalent bond. The remaining solution was removed by filtration and the product was dried under reduced pressure to obtain an immobilized lipase having a water content of about 10%.

EXAMPLE 2

An immobilized lipase having a water content of 5% was produced in the same manner as that of Example 1 except that a porous resin prepared by introducing epoxy groups into a matrix resin comprising styrene/divinylbenzene copolymer (Lewatit R260K having pore diameter of 29 nm and average particle diameter of 500μm; a product of Bayer) was used.

EXAMPLE 3

An immobilized lipase was produced in the same manner as that of Example 1 except that a porous resin prepared by introducing epoxy groups into a matrix resin prepared from polyacrylic acid (FP4000 having pore diameter of 55 nm and average particle diameter of 100 μm; a product of Japan Organo Co., Ltd.) was used.

COMPARATIVE EXAMPLES 1 to 3

An immobilized lipase was produced in the same manner as that of Example 1 except that a weakly basic anion exchange resin comprising a phenolic resin as the matrix (Duolite A-568 having particle diameter range of 200 to 400 μm; a product of Rohm & Haas Co.) (Comparative Example 1), an adsorbent resin comprising a phenolic resin as the matrix (Duolite S-762 having pore diameter range of 200 to 100 μm; a product of Rohm & Haas Co.) (Comparative Example 2) or an adsorbent resin comprising a styrene/divinylbenzene copolymer as the matrix (Diaion HP-40 having average particle diameter of 320 μm; a product of Mitsubishi Chemical Industries, Ltd.) (Comparative Example 3) was used.

The amount of the carried protein of each of immobilized lipases obtained in Examples 1 to 3 and Comparative Examples 1 to 3, and hydrolysis activity for olive oil are given in Table 1.

TABLE 1

| | Carrier | Amount of carried protein (mg/g-dry immobilized enzyme) | Hydrolysis activity (unit/g immobilized enzyme) | Degree of concentration |
|---|---|---|---|---|
| Ex. 1 | Lewatit R259K | 220 | 108300 | 1.4 |
| Ex. 2 | Lewatit R260K | 177 | 90100 | 1.5 |
| Ex. 3 | FP4000 | 102 | 84500 | 1.5 |
| Comp. Ex. 1 | Duolite A-568 | 244 | 26100 | 0.3 |
| Comp. Ex. 2 | Duolite S-762 | 167 | 88400 | 1.5 |
| Comp. Ex. 3 | Diaion HP-40 | 178 | 71900 | 1.2 |

EXAMPLE 4

200 mg (on dry basis) of the immobilized lipase prepared in Example 1 was added to 10 ml of a solution containing 50 mM of triolein and 50 mM of palmitic acid in hexane (water content: 100 ppm), and the reaction was conducted under stirring at 100 strokes/min at 50° C. 10, 20, 40, 60 and 120 min after initiation of the reaction, the concentration of palmitic acid and oleic acid in the reaction solution were determined. Transesterification activity was also determined using palmitic acid and triolein.

EXAMPLE 5

The transesterification reaction was conducted in the same manner as that of Example 4 except that the immobilized lipase prepared in Example 2 was used. The obtained transesterification activity is given in Table 2.

EXAMPLE 6

The transesterification reaction was conducted in the same manner as that of Example 4 except that the immobilized lipase prepared in Example 3 was used. The obtained transesterification activity is given in Table 2.

COMPARATIVE EXAMPLES 4 to 6

The transesterification reaction was conducted in the same manner as that of Example 4 except that the immobilized lipase prepared in Comparative Examples 1 to 3 was used.

COMPARATIVE EXAMPLE 7

The transesterification reaction was conducted in the same manner as that of Example 4 except that a commercially available immobilized lipase (Lipozyme IM 60; a product of NOVO NORDISK BIOINDUSTRY) was used.

The transesterification activities obtained in Examples 4 to 6 and Comparative Examples 4 to 7 are given in Table 2.

TABLE 2

| | Carrier | Transesterification activity (unit/g-immobilized enzyme) | Expression efficiency |
|---|---|---|---|
| Ex. 4 | Lewatit R259K | 282.4 | $2.61 \times 10^{-3}$ |
| Ex. 5 | Lewatit R260K | 247.2 | $2.74 \times 10^{-3}$ |
| Ex. 6 | FP 4000 | 218.4 | $2.58 \times 10^{-3}$ |
| Comp. Ex. 4 | Duolite A-568 | 11.2 | $0.43 \times 10^{-3}$ |
| Comp. Ex. 5 | Duolite S-762 | 24.7 | $0.28 \times 10^{-3}$ |
| Comp. Ex. 6 | Diaion HP-40 | 82.9 | $1.15 \times 10^{-3}$ |
| Comp. Ex. 7 | Lipozyme IM 60 | 145.3 | — |

EXAMPLE 7

An immobilized lipase was prepared in the same manner as that of Example 1 except that 1 g of 90,000 hydrolysis units/g of Lilipase A (from *Rhizopus japonicus*; a product of Nagase Sangyo & Co., Ltd.) was used as the lipase, and then the transesterification reaction was conducted in the same manner as that of Example 4.

COMPARATIVE EXAMPLE 8

An immobilized lipase was prepared in the same manner as that of Example 7 except that Duolite S-762, the resin of Comparative Example 2, was used as the immobilized lipase, and then the transesterification reaction was conducted in the same manner as that of Example 4.

The transesterification activities obtained in Example 7 and Comparative Example 8 are given in Table 3.

TABLE 3

| | Carrier | Transesterification activity (unit/g-immobilized enzyme) | Expression efficiency |
|---|---|---|---|
| Ex. 7 | Lewatit R259K | 203.4 | $5.21 \times 10^{-3}$ |
| Comp. Ex. 8 | Duolite S-762 | 10.4 | $0.80 \times 10^{-3}$ |

EXAMPLE 8

An immobilized lipase was prepared in the same manner as that of Example 1 except that 3 g of Lipase M (15,000 hydrolysis units/g) (derived from *Mucor javanicus*; a product of Amano Seiyaku Kabushiki Kaisha) was used as the lipase, and then the transesterification reaction was conducted in the same manner as that of Example 4.

EXAMPLE 9

An immobilized lipase was prepared in the same manner as that of Example 1 except that 1 g of Lipase PL (90,000 hydrolysis units/g) (from *Alcaligenes sp*; a product of The Meito Sangyo Co., Ltd.) was used as the lipase, and then the transesterification reaction was conducted in the same manner as that of Example 4.

EXAMPLE 10

An immobilized lipase was prepared in the same manner as that of Example 1 except that 1 g of Lipase OF (220,000 hydrolysis units/g) (derived from *Candida cylindracea*; a product of The Meito Sangyo Co., Ltd.) was used as the lipase, and then the transesterification reaction was conducted in the same manner as that of Example 4.

COMPARATIVE EXAMPLE 9

An immobilized lipase was prepared in the same manner as that of Example 1 except that 3 g of Lipase CES (34,000 hydrolysis units/g) (derived from *Pseudomonas sp*; a product of Amano Seiyaku K.K.) was used as the lipase, and then the transesterification reaction was conducted in the same manner as that of Example 4.

COMPARATIVE EXAMPLE 10

An immobilized lipase was prepared in the same manner as that of Example 1 except that 3 g of LipasS Sankyo (24,000 hydrolysis units/g) (from *Aspergillus niger*; a product of Sankyo Co., Ltd.) was used as the lipase, and then the transesterification reaction was conducted in the same manner as that of Example 4.

The transesterification activities obtained in Examples 8 to 10 and Comparative Examples 9 to 10 are given in Table 4.

TABLE 4

| | Enzyme | Transesterification activity (unit/g-immobilized enzyme) | Expression efficiency |
|---|---|---|---|
| Ex. 8 | Lipase M | 190.1 | $4.53 \times 10^{-3}$ |
| Ex. 9 | Lipase PL | 215.5 | $5.26 \times 10^{-3}$ |
| Ex. 10 | Lipase OF | 228.3 | $1.62 \times 10^{-3}$ |
| Comp. Ex. 9 | Lipase CES | 45.2 | $0.51 \times 10^{-3}$ |
| Comp. Ex. 10 | Lipase Sankyo | 29.8 | $0.89 \times 10^{-3}$ |

EXAMPLE 11 AND COMPARATIVE EXAMPLE 11

1 g of the immobilized lipase obtained in Example 1 and 1 g of the immobilized lipase obtained in Comparative Example 10 (lipase derived from *Aspergillus niger* was used) each were added to 100 g of a mixture of palm oil and rapeseed oil (1:1) (water content: 180 ppm), and the transesterification reaction was conducted under shaking at 100 strokes/min at 50° C. 2, 6 and 24 hours after, a sample was take n from the oil and the transesterification rate was determined (Example 11 and Comparative Example 11). The term "transesterification rate" herein indicates a value obtained by determining the triglyceride (having 53 carbon atoms) content before the initiation of the reaction and during the substantial reaction equilibrium, the value before the initiation being 0% and that during the substantial reaction equilibrium being 100%. The results are given in Table 5.

TABLE 5

| | | | Transesterification rate(%) | | |
|---|---|---|---|---|---|
| | Lipase | Carrier | 2 Hrs | 6 Hrs | 24 Hrs |
| Ex. 11 | Lipase | Lewatit R259K | 46.5 | 83.0 | 99.8 |

TABLE 5-continued

|  | Lipase | Carrier | Transesterification rate(%) | | |
|---|---|---|---|---|---|
|  |  |  | 2 Hrs | 6 Hrs | 24 Hrs |
| Comp. Ex. 11 | F-AP15 Lipase Sankyo | Lewatit R259K | 8.5 | 19.0 | 47.3 |

EXAMPLE 12 AND COMPARATIVE EXAMPLE 12

Transesterification reactions were conducted in the same manner as in Example 11 and comparative Example 11 except that a mixture of palm oil and rapeseed oil (1:1) was replased by a mixture of higholeic sunflower oil (oleic acid content 83%) and rapeseed oil (1:1). The resulting transesterification rates are shown in Table 6.

TABLE 6

|  | Lipase | Carrier | Transesterification rate(%) | | |
|---|---|---|---|---|---|
|  |  |  | 2 Hrs | 6 Hrs | 24 Hrs |
| Ex. 12 | Lipase F-AP15 | Lewatit R259K | 49.8 | 85.5 | 99.0 |
| Comp. Ex. 12 | Lipase Sankyo | Lewatit R259K | 9.5 | 20.1 | 49.6 |

EXAMPLE 13

Immobilized enzyme obtained in Example 1 was filled in a column of 100 ml to charge a mixture of palm oil and rapeseed oil (1:1) at a temperature of 65° C. at SV(space Velocity)=1 (1/1 column. Hr) in the column. After 400 hours, about 1 kg of transesterified oil was obtained out of the column and transesterification rate was determined. The transesterified oil was also subjected to wintering at a temperature of 5° C. to measure the yield of liquid part therefrom.

COMPARATIVE EXAMPLE 13

Example 13 was repeated except that immobilized enzyme obtained mn Example 1 was replaced by that obtained in comparative Example 1.

Resulting transesterification rate and yield of liquid part in Example 13 and comparative Example 13 are shown in Table 7.

TABLE 7

|  | Transesterification rate (%) | Yield of liquid part (%) |
|---|---|---|
| Ex. 13 | 81 | 71 |
| Comp. Ex. 13 | 42 | 54 |

EXAMPLE 14

Immobilized enzyme obtained in Example 1 was filled in a column of 100 ml to charge a mixture of higholeic sunflower oil (oleic acid content 83%) and stearic acid (98%) (1:1) at a temperature of 65° C. at SV=1 in the column. After 400 hours, about 1 kg of transesterified oil was obtained out of the column to determine the change in the triglyceride composition. The transesterification rate was calculated based on the change in triglyceride compositions before and after the reaction. Free fatty acids were removed from the transesterified oil by not more than 5% using distillation, after which two stage fraction was conducted with acetone at a temperature of 18° C. or 5° C. The middle melting part of the oil was purified to obtain cocoa substituted fat.

COMPARATIVE EXAMPLE 14

Example 14 was repeated except that immobilized enzyme obtained in Example 1 was replaced by that obtained in comparative Example 1.

The results are shown in Table 8.

TABLE 8

|  | Transesterification rate (%) | Yield of middle melting part (%) |
|---|---|---|
| Ex. 14 | 83 | 30 |
| Comp. Ex. 14 | 42 | 18 |

REFERENTIAL EXAMPLE 1

70 Weight % of divinylbenzene (DVB), 15 weight % of glycidyl methacrylate and 15 weight % of diethylaminoethyl (DEAE) methacrylate were copolymerized by an ordinary method to obtain a polymer carrier. The polymer carrier has pores of an average diameter of 12.3 nm and a pore volume of 0.5 cm$^3$/g.

EXAMPLE 15

1000 ml of 2 weight % of an aqueous solution of lipase FAP-15 derived from Rhizopus sp. (a product of Amano Seiyaku Kabushiki Kaisha: 150,000 u/g) was added to 100 g of the polymer carrier of referential Example 1 and stirred at a temperature of 25° C. for 4 hours to immobilize the lipase on the carrier. The remaining solution was removed by filtration and the product was washed with water and dried under reduced pressure to obtain 50 g of an immobilized lipase having a water content of 5%.

EXAMPLE 16

The procedure of Example 15 was repeated, except that lipase FAP-15 was replaced by lipase LP derived from Chromobacterium Viscosum (a product of Toyo Johzo Kabushiki Kaisha: 100,000 u/g) or lipase CES derived from Pseudomonas sp (a product of Amano Seiyaku Kabushiki Kaisha: 20,000 u/g). As a result, immobilized lipases LP① and CES ② were obtained.

EXAMPLE 17

The procedure of Example 15 was repeated, except that the polymer carrier of referential Example 1 was replaced by the following polymer carrier.

That is, the polymer carrier was prepared by adding 200 ml of 1% glutaric aldehyde solution (in 0.05M phosphoric acid buffer solution) to 100 g of porus polymer FE461 (a product of Japan Organo Co., Ltd.) having a primary amino group in which a matrix was methacryl resin, stirring the mixture at a room temperature for 1 hour, subjecting to filtration and washing with water, and drying it.

COMPARATIVE EXAMPLE 15

Immobilized lipase was prepared by the same method as in Example 15, except that the polymer carrier of referential Example 1 was replaced by a hydrophobic resin Duolite S861 having neither any functional group capable of binding lipase or phospholipase nor anion exchage group.

COMPARATIVE EXAMPLE 16

A commercially available Lipozyme (a product of NOVO NORDISK BIOINDUSTRY) in which a carrier was anion exchange resin was used as an immobilized lipase.

EXAMPLE 18

Transesterification activity and duration of life of the thus-obtained immobilized enzymes were determined by the following methods.

Transesterification Activity of Immobilized Enzyme

An up-take speed of palmitic acid into trioleln was measured at 50° C. The obtained speed (μmol/min/g of enzyme) was calculated as unit/ml of immobilized enzyme which was identified as the transesterification activity of immobilized enzyme.

Duration of Life for Immobilized Enzyme

Immobilized enzyme was filled in a column to charge a mixture of cotton seed oil and rapeseed oil (1:1) at SV (space velocity)=1 (1/1 column·hr) in the column. The degree of conversion was determined based on the change in the composition of tryglycerides composed of fatty acid having 50 carbon atoms and those composed of fatty acid having 52 carbon atoms, and total amount of oil to be charged in the column before the degree of conversion reaches 70% was identified as the duration of life for immobilized enzyme.

The results obtained are shown in Table 9.

TABLE 9

| Type of immo-<br>bilized enzyme | Transesterification activity<br>(unit/ml immobilized enzyme) | Duration<br>of life* |
|---|---|---|
| Example 15 | 90 | 1000 |
| Example 16 ① | 65 | 850 |
| ② | 60 | 850 |
| Example 17 | 90 | 900 |
| Com. Exam. 15 | 87 | 400 |
| Com. Exam. 16 | 46 | 250 |

*1 liter of raw oil/1 liter of immobilized enxyme

EXAMPLE 19

Example 18 was repeated except that a mixture of cotton seed oil and rapeseed oil (1:1), palmitic acid and triolein were replaced by a mixture of palm oil and rapeseed oil (1:1), myristic acid and palmolein, respectively. The results are shown in Table 10.

TABLE 10

| Type of immo-<br>bilized enzyme | Transesterification activity<br>(unit/ml immobilized enzyme) | Duration<br>of life* |
|---|---|---|
| Example 15 | 93 | 1000 |
| Example 16 ① | 68 | 800 |
| ② | 65 | 800 |
| Example 17 | 90 | 900 |
| Com. Exam. 15 | 85 | 400 |

TABLE 10-continued

| Type of immo-<br>bilized enzyme | Transesterification activity<br>(unit/ml immobilized enzyme) | Duration<br>of life* |
|---|---|---|
| Com. Exam. 16 | 48 | 250 |

*1 liter of raw oil/1 liter of immobilized enxyme

EXAMPLE 20

Immobilized enzyme obtained in Example 15 was filled in a column of 100 ml to charge a mixture of palm oil and rapeseed oil (1:1) at a temperature of 50° C. at SV=1 in the column. After 750 hours, about 1 kg of transesterified oil was obtained out of the column and transesterification rate was determined. The transesterified oil was also subjected to wintering at a temperature of 5° C. to measure the yield of liquid part therefrom.

COMPARATIVE EXAMPLE 17

Example 20 was repeated except that immobilized enzyme obtained in Example 15 was replaced by that obtained in comparative Example 16.

Resulting transesterification rate and yield of liquid part in Example 20 and comparative Example 17 are shown in Table 11.

TABLE 11

| | Transesterification<br>rate (%) | Yield of liquid<br>part (%) |
|---|---|---|
| Ex. 20 | 80 | 71 |
| Comp. Ex. 17 | 23 | 46 |

EXAMPLE 21

Immobilized enzyme obtained in Example 15 was filled in a column of 100 ml to charge a mixture of high oleic sunflower oil (oleic acid content 93%) and stearic acid (stearic acid content 98%) (1:1) at a temperature of 65° C. at SV=1 in the column. After 750 hours, about 1 kg of transesterified oil was obtained out of the column to determine the change in the trigtyceride composition. The transesterification rate was calculated based on the change in triglyceride compositions before and after the reaction. Free fatty acids were removed from the transesterified oil by not more than 5% using distillation, after which two stage fraction was conducted with acetone at a temperature of 18° C. or 5° C. The middle melting part of the oil was purified to botain cocoa substituted fat.

COMPARATIVE EXAMPLE 18

Example 21 was repeated except that immobilized enzyme obtained in Example 15 was replaced by that obtained in comparative Example 15.

The results are shown in Table 12.

TABLE 12

| | Transesterification<br>rate (%) | Yield of middle<br>melting part (%) |
|---|---|---|
| Ex. 21 | 84 | 30 |
| Comp. Ex. 18 | 30 | 16 |

EXAMPLE 22

Example 15 was repeated except that the aqueous solution of lipase FAP-15 was replaced by 1000 ml of an aqueous solution of phospholipase $A_2$ derived from porcine pancreas. 0.1 g of the resulting immobilized phospholipase was added to 10 ml of hexane solution (water content 0.01%) containing 0.443 g/ml of dioleilphosphatidylcholine and 50 mM of palmitic acid and shaked for 24 hours at a temperature of 50° C. after which the content of oleic acid in free acids was determined and found to be 12%.

EXAMPLE 23

20 g of rape seed oil and 100 ml of ion-exchanged water were added to 100 g of polymer carrier of reference Example 1 to shake them at a temperature of 30° C. for 30 minutes, after which the resultant was subjected to filtration and washing with water. To the resulting carrier were added 200 ml of phospholipase $A_2$ (from porcine pancreas, a product of NOVO NORDISK BIOINDUSTRY, 3700 u/ml) and the resultant was stirred at a temperature of 25° C. for 4 hours to immobilize the phospholipase on the carrier. The resulting immobilized carrier was subjected to filtration, washed with water and dried for 3 hours under a reduced pressure to obtain 50 g of immobilized phospholipase having a water content of 5%.

Hydrolysis activity of the immobilized phospholipase was 390 unit/g.

EXAMPLE 24

20 g of rape seed oil and 100 ml of ion-exchanged water were added to 100 g of polymer carrier of reference Example 1 to shake them at a temperature of 30° C. for 30 minutes, after which the resultant was subjected to filtration and washing with water. To the resulting carrier were added 1000 ml of 2% aqueous solution of lipase FAP-15 (from Rhizopus sp., a product of Amano Seiyaku Kabushiki Kaisha: 150,000 u/g) and the resultant was stirred at a temperature of 25° C. for 4 hours to immobilize the lipase on the carrier. The resulting immobilized lipase was subjected to filtration, washed with water and dried for 3 hours under a reduced pressure to obtain 50 g of immobilized lipase having a water content of 5%.

EXAMPLE 25

The procedure of Example 24 was repeated, except that lipase FAP-15 was replaced by lipase OF derived from *Candida cylindracea* (a product of Meito Sangyo Kabushiki Kaisha: 360,000 u/g), lipase LP derived from Chromobacterium Viscosum (a product of Toyo Johzo Kabushiki Kaisha: 100,000 u/g) or lipase CES derived from Pseudomonas sp (a product of Amano Seiyaku Kabushiki Kaisha: 20,000 u/g). As a result, immobilized lipases OF①, LP ② and CES ③ were obtained.

EXAMPLE 26

The procedure of Example 24 was repeated, except that rape seed oil was not used.

Transesterification activity and duration of life of the immobilized lipases obtained in Examples 24 to 26 were determined by the same method as in Example 19 and the results are shown in Table 13.

TABLE 13

| Type of immobilized enzyme | Transesterification activity (unit/ml immobilized enzyme) | Duration of life* |
|---|---|---|
| Example 24 | 199 | 4000 |
| Example 25 ① | 80 | 1800 |
| ② | 85 | 2100 |
| ③ | 90 | 2200 |
| Example 26 | 100 | 1000 |

*1 liter of raw oil/1 liter of immobilized enxyme

EXAMPLE 27

Immobilized enzyme obtained in Example 24 was filled in a column of 100 ml to charge a mixture of palm oil and rapeseed oil (1:1) at a temperature of 65° C. at SV=1 in the column. After 1500 hours, about 1 kg of transesterified oil was obtained out of the column and transesterification rate was determined. The transesterified oil was also subjected to wintering at a temperature of 5° C. to measure the yield of liquid part therefrom.

The above-described procedure was repeated except that immobilized enzyme obtained in Example 24 was replaced by that obtained in Example 26.

Resulting transesterification rate and yield of liquid in Example 27 are shown in Table 14.

TABLE 14

| Type of enzyme | Transesterification rate (%) | Yield of liquid (%) |
|---|---|---|
| Ex. 24 | 91 | 75 |
| Ex. 26 | 39 | 52 |

EXAMPLE 28 immobilized enzyme obtained in Example 24 was filled in a column of 100 ml to charge a mixture of high oleic sunflower oil (oleic acid content 93%) and stearic acid (stearic acid content 98%) (1:1) at a temperature of 65° C. at SV=1 in the column. After 1500 hours, about 1 kg of transesterified oil was obtained out of the column to determine the change in the triglyceride composition. The transesterification rate was calculated based on the change in triglyceride compositions before and after the reaction. Free fatty acids were removed from the transesterified oil by not more than 5% using distillation, after which two stage fraction was conducted with acetone at a temperature of 18° C. or 5° C. The middle melting part of the oil was purified to botain cocoa substituted fat.

The above-described procedure was repeated except that immobilized enzyme obtained in Example 24 was replaced by that obtained in Example 26.

The results are shown in Table 15.

TABLE 15

| Type of enzyme | Transesterification rate (%) | Yield of middle melting part (%) |
|---|---|---|
| Ex. 24 | 92 | 34 |
| Ex. 26 | 45 | 19 |

EXAMPLE 29

Example 24 was repeated except that the aqueous solution of lipase FAP-15 was replaced by 1000 ml of an aqueous solution of phospholipase $A_2$ derived from porcine pancreas. 0.1 g of the resulting immobilized phspholipase was added to 10 ml of hexane solution (water content 0.01%) containing 0.443 g/ml of dioleilphosphatidylcholine and 50 mM of palmitic acid and shaked for 24 hours at a temperature of 50° C., after which the content of oleic acid in free acids was determined and found to be 20%.

What is claimed is

1. A process for transesterification which comprises: transesterifying a fat, or a fat and a fatty acid, by contacting the fat, or fat and fatty acid with an immobilized lipase which comprises a lipase from a microorganism genus selected from the group consisting of Rhizopus, Mucor, Alcaligenes and Candida and immobilized on the surface of a carrier comprising a hydrophobic, insoluble organic polymer having pores of an average diameter of 10 nm or larger and tertiary amino groups and epoxy groups on the surface thereof.

2. The process of claim 1 wherein the fat and fatty acid are those produced from vegetables.

3. The process of claim 2 wherein the fat is selected from the group consisting of palm oil, a fractional oil obtained from palm oil, a hydrogenated oil obtained from palm oil and a mixture of palm oil plus a vegetable oil other than palm oil, said fractional oil or said hydrogenated oil.

4. The process of claim 1 wherein the transesterification is conducted in the presence of 50 to 2,000 ppm water.

5. The process of claim 1 wherein the transesterification is conducted at a temperature of 30° to 70° C.

6. The process of claim 1 wherein the insoluble organic polymer comprises a matrix resin selected from the group consisting of styrene/divinylbenzene copolymers, methacrylic ester resins, acrylic ester resins, polypropylenes, nylons and phenolic resins.

7. The process of claim 1 wherein the carrier is in the form of particles and at least 90 wt % of the carrier particles have a diameter of 50 to 1,000 µm.

8. The process of claim 1 wherein the epoxy groups are 1,2-epoxido groups.

9. The process of claim 1 wherein the immobilized lipase has a water content adjusted to 0.5 to 30 wt % by drying under reduced pressure.

10. The process of claim 1, wherein the immobilized lipase is prepared by bringing the carrier into contact with the lipase in the presence of a fatty acid, fat or oil.

11. A process for transesterification which comprises: transesterifying a fat, or a fat and fatty acid, or a phospholipid by contacting the fat, or fat and fatty acid, or phospholipid with an immobilized lipase or phospholipase which comprises phospholipase $A_2$, or a lipase from a microorganism genus selected from the group consisting of Rhizopus, Mucor, Alcaligenes and Candida, which has been immobilized on the surface of a polymer carrier in an aqueous solution, wherein said polymer carrier has tertiary amino groups and epoxy groups on the surface thereof.

12. The process of claim 4 wherein the lipase is a lipase from a microorganism genus selected from the group consisting of Rhizopus and Mucor.

13. The process of claim 11 wherein the transesterification is conducted in the presence of 50 to 2,000 ppm water.

14. The process of claim 11 wherein the transesterification is conducted at a temperature of 30° to 70° C.

15. The process of claim 11 wherein the phospholipid is lecithin.

16. The process of claim 11 wherein the carrier is in the form of particles and the fat is selected from the group consisting of palm oil, a fractional oil obtained from palm oil, a hydrogenated oil obtained from palm oil and a mixture of palm oil plus a vegetable oil other than palm oil, said fractional oil or said hydrogenated oil.

17. The process of claim 11 wherein the polymer carrier comprises a matrix resin selected from the group consisting of styrene/divinylbenzene copolymers, methacrylic ester resins, acrylic ester resins, polypropylenes, nylons and phenolic resins.

18. The process of claim 11 wherein the carrier is in the form of particles and at least 90 wt % of the carrier particles have a diameter of 50 to 1,000 µm.

19. The process of claim 11 wherein the epoxy groups are 1,2-epoxido groups.

20. The process of claim 11 wherein the immobilized lipase has a water content adjusted to 0.5 to 30 wt % by drying under reduced pressure.

21. The process of claim 11, wherein the immobilized lipase or phospholipase is prepared by bringing the carrier into contact with the lipase or phospholipase $A_2$ in the presence of a fatty acid, fat or oil.

* * * * *